(12) United States Patent
Ypema et al.

(10) Patent No.: US 8,916,597 B2
(45) Date of Patent: Dec. 23, 2014

(54) USE OF PYRACLOSTROBIN AS SAFENER FOR TRITICONAZOLE FOR CONTROLLING HARMFUL FUNGI

(75) Inventors: Hendrik Ypema, Cary, NC (US); Andreas Hopf, Neustadt (DE); Nathan Froese, Winkler (CA); Reinhard Stierl, Kaohsiung County (TW)

(73) Assignee: BASF SE, Ludwigshafen (DE)

( * ) Notice: Subject to any disclaimer, the term of this patent is extended or adjusted under 35 U.S.C. 154(b) by 485 days.

(21) Appl. No.: 12/084,238

(22) PCT Filed: Nov. 6, 2006

(86) PCT No.: PCT/EP2006/068103
§ 371 (c)(1),
(2), (4) Date: Apr. 28, 2008

(87) PCT Pub. No.: WO2007/054471
PCT Pub. Date: May 18, 2007

(65) Prior Publication Data
US 2009/0291994 A1 Nov. 26, 2009

Related U.S. Application Data

(60) Provisional application No. 60/735,195, filed on Nov. 10, 2005.

(51) Int. Cl.
*A01N 43/64* (2006.01)
*A01P 3/00* (2006.01)
*A01N 43/653* (2006.01)

(52) U.S. Cl.
CPC ..................................... *A01N 43/653* (2013.01)
USPC ....................................................... 514/383

(58) Field of Classification Search
None
See application file for complete search history.

(56) References Cited

U.S. PATENT DOCUMENTS

| | | | |
|---|---|---|---|
| 5,256,683 A | 10/1993 | Hutt et al. | |
| 5,380,743 A | 1/1995 | Hutt et al. | |
| 5,689,517 A | 11/1997 | Ruparel | |
| 5,693,918 A | 12/1997 | Bremigan et al. | |
| 6,054,592 A | 4/2000 | Muller et al. | |
| 6,369,090 B1 * | 4/2002 | Schelberger et al. | 514/384 |
| 2005/0032903 A1 * | 2/2005 | Suarez-Cervieri et al. | 514/620 |
| 2005/0032905 A1 | 2/2005 | Reo et al. | |
| 2008/0064601 A1 | 3/2008 | Casanello et al. | |

FOREIGN PATENT DOCUMENTS

| | | |
|---|---|---|
| CA | 2 558 062 A1 | 10/2005 |
| EP | 0 378 953 A1 | 7/1990 |
| EP | 0 804 421 | 1/1996 |
| WO | WO-98/54969 A | 12/1998 |
| WO | WO02/069715 | 9/2002 |
| WO | WO-02/069715 A2 | 9/2002 |
| WO | WO-2005/094583 A1 | 10/2005 |
| WO | WO-2007/031283 A2 | 3/2007 |

OTHER PUBLICATIONS

Ghannoum et al. in Clinical Microbiology Reviews 12(4), 501-517 (1999).*
Montfort, Francoise. et al. "Effects of Two Triazole Seed Treatments, Triticonazole and Triadimenol, on Growth and Development of Wheat", Pestic. Sci. vol. 46, 1996, p. 315-322. XP-002484173.
Derwent-2007-327690/31, Sep. 13, 2005.
Derwent-2003-122145/12, Mar. 6, 2001.

* cited by examiner

*Primary Examiner* — Dennis Heyer
(74) *Attorney, Agent, or Firm* — Brinks Gilson & Lione

(57) ABSTRACT

(1) Use of pyraclostrobin of the formula I

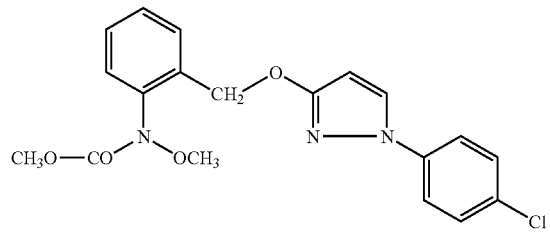

as safener for
(2) triticonazole of the formula II

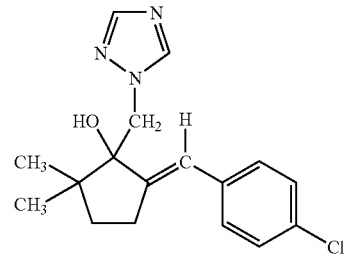

or salts or adducts thereof for controlling harmful fungi.
The use of the compounds I and II in a process for controlling harmful fungi using mixtures of the compounds I and II and the use of the compounds I and II for preparing such mixtures, and also compositions comprising such mixtures.

13 Claims, No Drawings

USE OF PYRACLOSTROBIN AS SAFENER FOR TRITICONAZOLE FOR CONTROLLING HARMFUL FUNGI

The present invention relates to
(1) the use of pyraclostrobin of the formula I

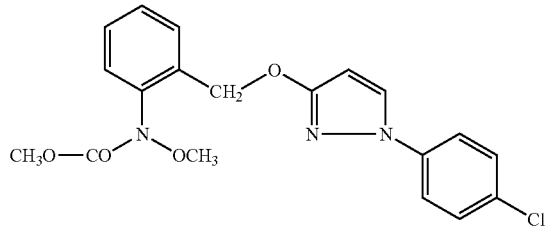

as safener for
(2) triticonazole of the formula II

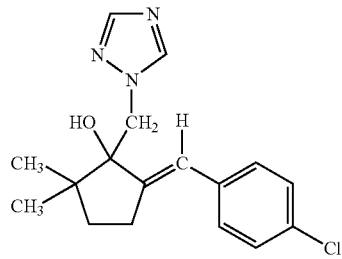

or salts or adducts thereof for controlling harmful fungi.

Moreover, the invention relates to the use of the compounds I and II in a method for controlling harmful fungi using mixtures of the compounds I and II and to the use of the compounds I and II for preparing such mixtures, and also to compositions comprising these mixtures.

Pyraclostrobin of the formula I is known from EP-A 0 804 421.

Triticonazole of the formula II is described in EP-A 0 378 953.

Mixtures of pyraclostrobin of the formula I and triticonazole of the formula II with other fungicides are also known, from WO 98/54969.

DE 102 00 402 9338.4 discloses the use of triticonazole in a mixture with a strobilurin for controlling infections of soybeans by rust.

Montfort, F. et al., Pesticide Science 46(4), 1996, 1996, pp. 315-322 discloses, that a negative effect on plant growth may occur when triticonazole is used for treating seed or crop plants. A negative effect during the treatment with triticonazole may be a strongly reduced longitudinal growth, for example. This effect has been described for the crop plant wheat.

It was an object of the present invention to provide a safener which eliminates the negative effects of the triticonazole with respect to plant growth, at the same fungicidal action.

We have found that this object is achieved by the use, defined at the outset, of pyraclostrobin as safener for triticonazole for controlling harmful fungi. Moreover, we have found that pyraclostrobin and triticonazole can be applied simultaneously, that is jointly or separately. Furthermore, it has been found that pyraclostrobin and triticonazole can be used for preparing a composition.

Pyraclostrobin of the formula I

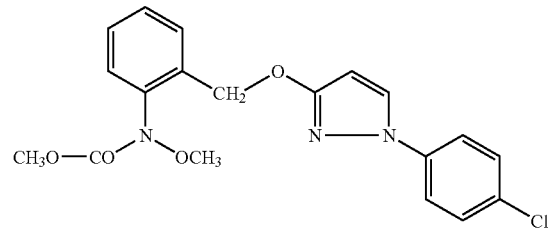

is described in EP-A 0 804 421.

Triticonazole of the formula II

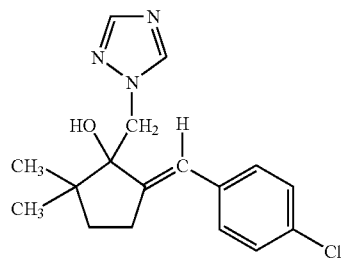

is described in EP-A 0 378 953.

Owing to the basic character of its nitrogen atoms, the compound II is capable of forming salts or adducts with inorganic or organic acids and with metal ions, respectively.

Examples of inorganic acids are hydrohalic acids, such as hydrogen fluoride, hydrogen chloride, hydrogen bromide and hydrogen iodide, sulfuric acid, phosphoric acid and nitric acid.

Suitable organic acids are, for example, formic acid, carbonic acid, and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or disulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or diphosphonic acids (aromatic radicals, such as phenyl and naphthyl, which carry one or two phosphoric acid radicals), where the alkyl or aryl radicals may carry further substituents, for example p-toluenesulfonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminum, tin and lead and also of the elements of transition groups one to eight, in particular chromium, manganese, iron, cobalt, nickel, copper, zinc, and others. Particular preference is given to the metal ions of the elements of transition groups of the fourth period. The metal ions can be present in the various valencies that they can assume.

As described at the outset, in many crops, dressing of the seed with fungicides delays or reduces emergence and results in a poorer establishment of the stand when the cultivation is started.

The use of the mixtures of the compounds I and II, or the simultaneous, that is joint or separate, use of one of the compounds I and II, are/is distinguished in that these negative effects on the plants which, depending on the dosage, may also occur with triticonazole or pyraclostrobin, do not occur, or are not as pronounced. In addition, the mixtures have excellent activity against a broad spectrum of phytopathogenic fungi, in particular from the classes of the Ascomycetes, Basidiomycetes, Deuteromycetes and Peronosporomycetes (syn. Oomycetes). Some of them are systemically active and can be used in crop protection as foliar fungicides, as fungicides for seed dressing and as soil fungicides.

They are particularly important for controlling a multitude of fungi on various cultivated plants, such as bananas, cotton, vegetable species (for example cucumbers, beans, tomatoes and cucurbits), barley, grass, oats, coffee, potatoes, corn, fruit species, rice, rye, legumes (for example soy beans, peas, beans, lentils), grapevines, wheat, ornamental plants, sugar cane and also on a large number of seeds.

They are especially suitable for controlling the following plant diseases:

Alternaria species on vegetables, rapeseed, sugar beet and fruit and rice,
Aphanomyces species on sugar beet and vegetables,
Bipolaris and Drechslera species on corn, cereals, rice and lawns,
Blumeria graminis (powdery mildew) on cereals,
Botrytis cinerea (gray mold) on strawberries, vegetables, flowers and grape vines,
Bremia lactucae on lettuce,
Cercospora species on corn, soybeans, rice and sugar beet,
Cochliobolus species on corn, cereals, rice (e.g., Cochliobolus sativus on cereals, Cochliobolus miyabeanus on rice),
Colletotricum species on soybeans and cotton,
Drechslera species on cereals and corn,
Exserohilum species on corn,
Erysiphe cichoracearum and Sphaerotheca fuliginea on cucurbits,
Fusarium and Verticillium species on various plants,
Gaeumanomyces graminis on cereals,
Gibberella species on cereals and rice (e.g., Gibberella fujikuroi on rice),
Grain staining complex on rice,
Helminthosporium species on corn and rice,
Michrodochium nivale on cereals,
Mycosphaerella species on cereals, bananas and peanuts,
Phakopsara pachyrhiziand Phakopsara meibomiae on soybeans,
Phomopsis species on soybeans and sunflowers,
Phytophthora infestans on potatoes and tomatoes,
Plasmopara viticola on grapevines,
Podosphaera leucotricha on apples,
Pseudocercosporella herpotrichoides on cereals,
Pseudoperonospora species on hops and cucurbits,
Puccinia species on cereals and corn,
Pyrenophora species on cereals,
Pyricularia oryzae, Corticium sasakii, Sarocladium oryzae, S. attenuatum, Entyloma oryzae on rice,
Pyricularia grisea on lawns and cereals,
Pythium spp. on lawns, rice, corn, cotton, rapeseed, sunflowers, sugar beet, vegetables and other plants,
Rhizoctonia species on cotton, rice, potatoes, lawns, corn, rapeseed, potatoes, sugar beet, vegetables and other plants,
Sclerotinia species on rapeseed and sunflowers,
Septoria tritici and Stagonospora nodorum on wheat,
Erysiphe (syn. Uncinula) necator on grapevines,
Setospaeria species on corn and lawns,
Sphacelotheca reilinia on corn,
Thievaliopsis species on soybeans and cotton,
Tilletia species on cereals,
Ustilago species on cereals, corn and sugar beet, and
Venturia species (scab) on apples and pears.

The compounds I and II an also be used for controlling harmful fungi such as Paecilomyces variotii in the protection of materials (for example wood, paper, paint dispersions, fibers or fabrics) and in the protection of stored products.

The compounds I and II can be applied simultaneously, that is jointly or separately, or in succession, the sequence, in the case of separate application, generally not having any effect on plant growth and the result of the control measures.

During use according to the invention, it is preferred to employ the pure active compounds I and II, to which further active compounds against harmful fungi or against other pests, such as insects, arachnids or nematodes, or else herbicidal or growth-regulating active compounds or fertilizers can be added according to need.

Usually, mixtures of the compounds I and II are used. However, in certain cases mixtures of the compounds I and II with, if appropriate, a plurality of active components may be advantageous, such as, for example, mixtures of the compounds I and II with further fungicides.

The mixing ratio (weight ratio) of the compounds I and II is chosen such that the described safener action occurs, for example compound I:compound II such as 100:1 to 1:100, in particular from 10:1 to 1:10, for example from 5:1 to 1:5, in particular from 3:1 to 1:3, preferably from 2:1 to 1:2. The safener action of the mixture manifests itself in that the negative effect of the triticonazole on the growth of the plants is absent or not as pronounced.

The further active components are, if desired, added in a ratio of from 20:1 to 1:20 to the compounds I and II.

Depending on the type of compound and the desired effect, the application rates of the mixtures used are, especially agricultural crop areas, from 5 g/ha to 2000 g/ha, preferably from 20 to 900 g/ha, in particular from 50 to 750 g/ha.

Correspondingly, the application rates for the compound I are generally from 1 to 1000 g/ha, preferably from 10 to 900 g/ha, in particular from 20 to 750 g/ha.

Correspondingly, the application rates for the active compound II are generally from 1 to 1000 g/ha, preferably from 10 to 900 g/ha, in particular from 40 to 750 g/ha.

In the treatment of seed, application rates of mixture are generally from 1 to 1000 g/100 kg of seed, preferably from 1 to 750 g/100 kg, in particular from 5 to 500 g/100 kg.

The use according to the invention of the compounds I and II in the method for controlling harmful fungi is carried out by the separate or joint application of the compounds I and II or a mixture of the compounds I and II by spraying or dusting the seeds, the plants or the soil before or after sowing of the plants or before or after emergence of the plants.

When using the compounds I and II according to the invention, they can be converted into the customary formulations, for example solutions, emulsions, suspensions, dusts, powders, pastes and granules. The use form depends on the particular intended purpose; in each case, it should ensure a fine and even distribution of the compounds I and II.

The formulations are prepared in a known manner, for example by extending the active compound with solvents and/or carriers, if desired using emulsifiers and dispersants. Solvents/auxiliaries suitable for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable for use as surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. The active compounds are employed in a purity of from 90% to 100%, preferably 95% to 100% (according to NMR spectrum).

The following are examples of formulations: 1. Products for dilution with water

A) Water-Soluble Concentrates (SL)

10 parts by weight of a compound according to the invention are dissolved in 90 parts by weight of water or of a water-soluble solvent. As an alternative, wetting agents or other auxiliaries are added. The active compound dissolves upon dilution with water. This gives a formulation having an active compound content of 10% by weight.

B) Dispersible Concentrates (DC)

20 parts by weight of a compound according to the invention are dissolved in 70 parts by weight of cyclohexanone with addition of 10 parts by weight of dispersant, for example polyvinylpyrrolidone. Dilution with water gives a dispersion. The active compound content is 20% by weight.

C) Emulsifiable Concentrates (EC)

15 parts by weight of a compound according to the invention are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D) Emulsions (EW, EO)

25 parts by weight of a compound according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (e.g. Ultraturrax) and made into a homogeneous emulsion. Dilution with water gives an emulsion. The formulation has an active compound content of 25% by weight.

E) Suspensions (SC, OD)

In an agitated ball mill, 20 parts by weight of a compound according to the invention are comminuted with addition of 10 parts by weight of dispersants and wetting agents and 70 parts by weight of water or an organic solvent to give a fine active compound suspension. Dilution with water gives a stable suspension of the active compound. The active compound content in the formulation is 20% by weight.

F) Water-Dispersible Granules and Water-Soluble Granules (WG, SG)

50 parts by weight of a compound according to the invention are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution of the active compound. The formulation has an active compound content of 50% by weight.

G) Water-Dispersible Powders and Water-Soluble Powders (WP, SP)

75 parts by weight of a compound according to the invention are ground in a rotor-stator mill with addition of 25 parts by weight of dispersants, wetting agents and silica gel. Dilution with water gives a stable dispersion or solution of the active compound. The active compound content of the formulation is 75% by weight.

2. Products to be Applied Undiluted

H) Dustable powders (DP)

5 parts by weight of a compound according to the invention are ground finely and mixed intimately with 95 parts by weight of finely divided kaolin. This gives a dustable product having an active compound content of 5% by weight.

J) Granules (GR, FG, GG, MG)

0.5 part by weight of a compound according to the invention is ground finely and associated with 99.5 parts by weight of carriers. Current methods are extrusion, spray-drying or the fluidized bed. This gives granules to be applied undiluted having an active compound content of 0.5% by weight.

K) ULV Solutions (UL)

10 parts by weight of a compound according to the invention are dissolved in 90 parts by weight of an organic solvent, for example xylene. This gives a product to be applied undiluted having an active compound content of 10% by weight.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), it being possible thereby to apply formulations comprising over 95% by weight of active compound, or even to apply the active compound without additives.

Oils of various types, wetters, adjuvants, may be added to the active compounds, even, if appropriate, not until immediately prior to use (tank mix). These agents are typically admixed with the compositions according to the invention in a weight ratio of from 1:100 to 100:1, preferably from 1:10 to 10:1.

The compounds I and II or the mixtures or the corresponding formulations are applied by treating the harmful fungi, the plants, seeds, soils, areas, materials or spaces to be kept free from them with a fungicidally effective amount of the mixture or, in the case of separate application, of the compounds I and II. Application can be carried out before or after infection by the harmful fungi.

The safener action of the compounds I and II was demonstrated by the tests below.

Seeds were treated with the two active compounds individually or with mixtures of both active compounds, and the development of the plants was then observed. When the mixtures were used, the negative effects of one or both mixing partners in the case of individual application were, if at all, observed at a reduced level.

Seed Treatment of Bentgrass

Seeds of bentgrass were seed-treated with the products and concentrations listed. Triticonazol and Pyraclostrobin were used as 200 g/l FS-formulation.

Treated sees were planted at the day of treatment and then kept under humid conditions in the greenhouse. 9 days after plating the ground coverage by emerged plants were estimated in percentage.

| Treatment | Concentration | % covered ground |
|---|---|---|
| untreated | — | 8.5% |
| Triticonazol | 10 g a.i./100 kg seed | 5.3% |
| Pyraclostrobin | 10 g a.i./100 kg seed | 13.3% |
| Triticonazol & Pyraclostrobin | 10 g a.i./100 kg seed & 10 g a.i./100 kg seed | 9.0% |

The data show that the negative effect of TTZ can be compensated by Pyraclostrobin.

The invention claimed is:

1. A method for controlling harmful fungi comprising applying to the harmful fungi, plants, seeds, soils, areas, materials or spaces to be free from the harmful fungi a fungicidally effective amount of a mixture comprising, or in the case of separate application, pyraclostrobin of the formula I

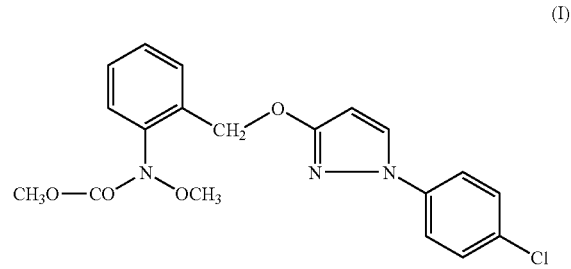

in an amount effective as a safener and
(2) triticonazole of the formula II

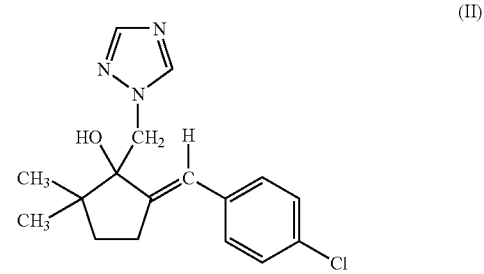 [SMILES: CC1(C)CC/C(=C\c2ccc(Cl)cc2)C1(O)Cn1cncn1]

or salts or adducts thereof.

2. The method according to claim 1, wherein the weight ratio of pyraclostrobin of the formula I to triticonazole of the formula II is from 100:1 to 1:100.

3. The method according to claim 1, which comprises treating the fungi, their habitat or the plants, seeds, soils, areas, materials or spaces to be kept free from them with pyraclostrobin of the formula I and triticonazole of the formula II.

4. The method according to claim 3, wherein the compounds of the formulae I and II are applied simultaneously, that is together or separately, or in succession.

5. The method according to claim 3 or 4, wherein the compounds of the formulae I and II are applied in an amount of from 5 g/ha to 2000 g/ha.

6. The method according to claim 3 or 4, wherein the compounds I and II are applied in an amount of from 1 g to 1000 g per 100 kg of seed.

7. The method of claim 1, wherein the compounds of the formulae I and II are applied simultaneously, that is together or separately, or in succession.

8. The method according to claim 4 wherein the compounds of the formulae I and II are applied in an amount of from 5 g/ha to 2000 g/ha.

9. The method of claim 1, wherein the compounds of the formulae I and II are applied in an amount of from 5 g/ha to 2000 g/ha.

10. The method according to claim 4 wherein the compounds I and II are applied in an amount of from 1 g to 1000 g per 100 kg of seed.

11. The method of claim 1, wherein the compounds I and II are applied in an amount of from 1 g to 1000 g per 100 kg of seed.

12. A composition comprising pyraclostrobin of the formula I

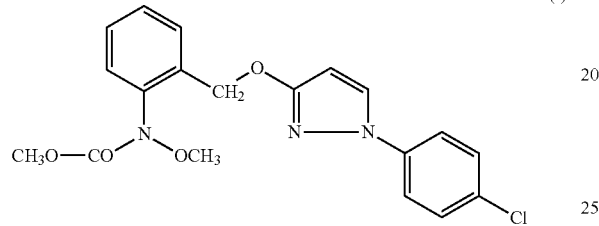

(I)

and triticonazole of the formula II

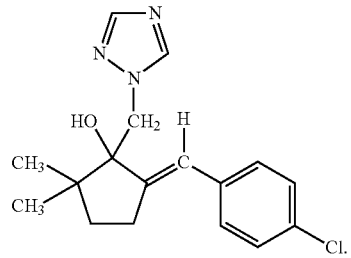

(II)

13. The composition according to claim 12, wherein the composition comprises, in addition to the compounds of the formulae I and II, a solid or liquid carrier.

* * * * *